(12) United States Patent
Hashimoto et al.

(10) Patent No.: US 11,119,199 B2
(45) Date of Patent: Sep. 14, 2021

(54) ACOUSTIC WAVE IMAGE GENERATION APPARATUS AND ACOUSTIC WAVE IMAGE GENERATION METHOD

(71) Applicant: FUJIFILM Corporation, Tokyo (JP)

(72) Inventors: Atsushi Hashimoto, Kanagawa (JP); Kaku Irisawa, Kanagawa (JP); Yukiya Miyachi, Kanagawa (JP)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

(21) Appl. No.: 16/054,466

(22) Filed: Aug. 3, 2018

(65) Prior Publication Data

US 2018/0341011 A1 Nov. 29, 2018

Related U.S. Application Data

(63) Continuation of application No. PCT/JP2017/004072, filed on Feb. 3, 2017.

(30) Foreign Application Priority Data

Feb. 8, 2016 (JP) .............................. JP2016-022210

(51) Int. Cl.
*G01S 1/52* (2006.01)
*G01S 7/52* (2006.01)
(Continued)

(52) U.S. Cl.
CPC ............ *G01S 7/52017* (2013.01); *A61B 8/13* (2013.01); *G01N 29/0672* (2013.01); *G01N 29/2418* (2013.01); *A61B 5/0095* (2013.01)

(58) Field of Classification Search
CPC combination set(s) only.
See application file for complete search history.

(56) References Cited

U.S. PATENT DOCUMENTS 4,463,608 A * 8/1984 Takeuchi ............ G01S 15/8965
73/602
6,080,107 A 6/2000 Poland
(Continued)

FOREIGN PATENT DOCUMENTS

CN 101472520 A 7/2009
CN 101563035 A 10/2009
(Continued)

OTHER PUBLICATIONS

Park, (High frequency photoacoustic imaging for in vivo visualizing blood flow of zebrafish heart, Jun. 12, 2013) (Year: 2013).*
(Continued)

*Primary Examiner* — Isam A Alsomiri
*Assistant Examiner* — Amie M Ndure
(74) *Attorney, Agent, or Firm* — Birch, Stewart, Kolasch & Birch, LLP (57) ABSTRACT

An acoustic wave image generation apparatus for generating a photoacoustic image and a Doppler image is provided with a setting unit that sets a region of interest in the Doppler image, and a receiving-aperture controlling unit that sets receiving apertures of an acoustic wave detection probe for detecting photoacoustic waves to apertures smaller than all receiving apertures that the acoustic wave detection probe has, on the basis of a size of the region of interest, and for setting positions of the receiving apertures on the basis of a position of the set region of interest.

12 Claims, 5 Drawing Sheets

(51) Int. Cl.
*A61B 8/13* (2006.01)
*G01N 29/06* (2006.01)
*G01N 29/24* (2006.01)
*A61B 5/00* (2006.01)

(56) References Cited

U.S. PATENT DOCUMENTS

| | | | |
|---|---|---|---|
| 2006/0241464 A1* | 10/2006 | Ohtake | A61B 8/06 600/457 |
| 2009/0054763 A1* | 2/2009 | Wang | A61B 5/0059 600/425 |
| 2009/0187099 A1 | 7/2009 | Burcher | |
| 2010/0016717 A1 | 1/2010 | Dogra et al. | |
| 2011/0201914 A1* | 8/2011 | Wang | A61B 5/0059 600/407 |
| 2011/0307181 A1* | 12/2011 | Nagae | G01S 7/52047 702/19 |
| 2012/0065490 A1* | 3/2012 | Zharov | A61B 5/0059 600/407 |
| 2012/0157837 A1* | 6/2012 | Nagata | G01N 29/0672 600/437 |
| 2012/0200845 A1* | 8/2012 | Rousseau | A61B 5/0093 356/72 |
| 2012/0203103 A1* | 8/2012 | Wang | A61B 5/0095 600/431 |
| 2013/0039147 A1* | 2/2013 | Witte | A61B 5/0093 367/7 |
| 2013/0199300 A1 | 8/2013 | Abe | |
| 2013/0245406 A1 | 9/2013 | Wang et al. | |
| 2014/0024918 A1* | 1/2014 | Hirota | A61B 5/7425 600/407 |
| 2014/0142404 A1* | 5/2014 | Wang | A61B 8/4416 600/324 |
| 2014/0148682 A1 | 5/2014 | Hirota et al. | |
| 2014/0182385 A1* | 7/2014 | Oh | A61B 5/0095 73/655 |
| 2014/0194740 A1 | 7/2014 | Stein et al. | |
| 2014/0198606 A1 | 7/2014 | Morscher et al. | |
| 2014/0276059 A1* | 9/2014 | Sheehan | A61B 8/12 600/443 |
| 2015/0011872 A1* | 1/2015 | Koh | A61B 5/4887 600/424 |
| 2015/0148655 A1* | 5/2015 | Haupt | A61B 8/10 600/407 |
| 2015/0262553 A1 | 9/2015 | Nam et al. | |
| 2015/0265156 A1 | 9/2015 | Tanaka | |
| 2016/0066893 A1* | 3/2016 | Cho | A61B 8/54 600/459 |
| 2017/0112474 A1 | 4/2017 | Burcher | |
| 2017/0188840 A1 | 7/2017 | Nanaumi | |

FOREIGN PATENT DOCUMENTS

| | | |
|---|---|---|
| CN | 103845078 A | 6/2014 |
| CN | 104905812 A | 9/2015 |
| JP | 2012-223367 A | 11/2012 |
| JP | 2012-254284 A | 12/2012 |
| JP | 2013-158531 A | 8/2013 |
| JP | 2014-136102 A | 7/2014 |
| JP | 2014-136103 A | 7/2014 |
| JP | 2015-150238 A | 8/2015 |
| JP | 2015-181660 A | 10/2015 |
| WO | WO 2014/070993 A1 | 5/2014 |

OTHER PUBLICATIONS

Extended European Search Report for European Application No. 17750182.2, dated Dec. 21, 2018.
International Preliminary Report on Patentability and Written Opinion of the International Searching Authority (forms PCT/IB/373, PCT/ISA/237 and PCT/IB/326), dated Aug. 23, 2018, for International Application No. PCT/JP2017/004072, with an English translation of the Written Opinion.
International Search Report (form PCT/ISA/210), dated May 16, 2017, for International Application No. PCT/JP2017/004072, with an English translation.
Chinese Office Action and Search Report for Chinese Application No. 201780010312.2, dated Jun. 24, 2020, with an English translation.
Chinese Office Action and Search Report, dated Nov. 27, 2020, for Chinese Application No. 201780010312.2, with English translations.

* cited by examiner

ACOUSTIC WAVE IMAGE GENERATION APPARATUS AND ACOUSTIC WAVE IMAGE GENERATION METHOD

CROSS-REFERENCE TO RELATED APPLICATIONS

This application is a continuation application of International Application No. PCT/JP2017/004072, filed Feb. 3, 2017, the disclosure of which is incorporated herein by reference in its entirety. Further, this application claims priority from Japanese Patent Application No. 2016-022210, filed Feb. 8, 2016, the disclosure of which is incorporated herein by reference in its entirety.

BACKGROUND

1. Technical Field

The present invention relates to an apparatus for generating an acoustic wave image and a method for generating an acoustic wave image.

2. Related Art

A noninvasive measurement method based on the photoacoustic effect has attracted attention in recent years. This measurement method includes emitting pulsed light having a certain appropriate wavelength (for example, within the wavelength range of visible light, near-infrared light, or intermediate infrared light) to a subject, detecting photoacoustic waves that are elastic waves produced as a result of absorption of energy of the pulsed light by an absorbing material in the subject, and quantitatively measuring the concentration of the absorbing material. Examples of the absorbing material in the subject include glucose and hemoglobin contained in blood. A technology for detecting photoacoustic waves and generating a photoacoustic image based on photoacoustic wave detection signals is called photoacoustic imaging (PAI) or photo acoustic tomography (PAT).

For example, JP2013-158531A and JP2015-181660A disclose apparatuses for generating a photoacoustic image through photoacoustic imaging. As disclosed in JP2015-181660A, a photoacoustic image generation apparatus of this type is often configured to also generate a so-called reflected ultrasound image.

An apparatus that generates a reflected ultrasound image typically generates a tomographic image or the like of the inside of the subject on the basis of signals obtained by detecting reflected acoustic waves, which are acoustic waves (mostly ultrasonic waves) emitted to the subject and reflected within the subject. Further, as disclosed in JP2014-136103A, another well-known apparatus performs frequency analysis of velocity information from reflected ultrasonic detection signals, extracts blood flow, tissues, and contrast medium echo components by using the Doppler effect, and generates a Doppler image indicating, for example, blood flow portions. The Doppler image can be commonly created by using an apparatus that generates a photoacoustic image, as disclosed in JP2014-136103A.

In contrast, a photoacoustic image generation apparatus typically emits light such as laser light to the subject and generates a photoacoustic image indicating tissues and the like inside the subject on the basis of signals obtained by detecting photoacoustic waves generated from within the subject which has absorbed the light.

An image generated on the basis of reflected ultrasonic detection signals and an image generated on the basis of photoacoustic wave detection signals are collectively referred to herein as an acoustic wave image.

SUMMARY

As described above, a conventional acoustic wave image generation apparatus capable of generating both an image generated on the basis of reflected ultrasonic detection signals and an image generated on the basis of photoacoustic wave detection signals is required to allow simultaneous observation of a Doppler image and a photoacoustic image. For example, blood flow portions and the like are visible on a Doppler image, and blood vessels are visible on a photoacoustic image by visualizing hemoglobin and the like in blood.

When a Doppler image and a photoacoustic image can be observed simultaneously in the way described above, it is desirable that both images can be observed with real-time imaging. However, the real-time acquisition of photoacoustic images is less achieved than that of Doppler images. That is, whereas it can be ensured that the repetition frequency for Doppler image generation is 30 Hz (with the frame rate being 30 images/second), the repetition frequency for photoacoustic image generation is limited to about 10 Hz (with the frame rate being 10 images/second) because the generation of a photoacoustic image requires emission of light to the subject.

The present invention has been made in view of the foregoing issues, and it is an object of the present invention to provide an acoustic wave image generation apparatus and method that enable generation of an image based on reflected ultrasonic detection signals and an image based on photoacoustic wave detection signals, in which a frame rate at which a photoacoustic image is generated is maintained high.

An acoustic wave image generation apparatus according to an aspect of the present invention is an acoustic wave image generation apparatus for generating a photoacoustic image on the basis of signals obtained by detecting, using an acoustic wave detection probe, photoacoustic waves produced from within a subject that has received light emitted to the subject and for generating a Doppler image concerning the subject, the acoustic wave image generation apparatus including:

a setting unit that sets a region of interest in the Doppler image; and a receiving-aperture controlling unit that sets receiving apertures of the acoustic wave detection probe for detecting the photoacoustic waves to apertures smaller than all receiving apertures that the acoustic wave detection probe has, on the basis of a size of the set region of interest, and for setting positions of the receiving apertures of the acoustic wave detection probe for detecting the photoacoustic waves, on the basis of a position of the set region of interest.

In the acoustic wave image generation apparatus according to an aspect of the present invention, desirably, as the acoustic wave detection probe, an acoustic wave detection probe configured such that a plurality of acoustic wave transducers capable of detecting the photoacoustic waves are arranged is used, and the receiving-aperture controlling unit blocks photoacoustic wave detection signals output from at least a part of acoustic wave transducers other than acoustic wave transducers to be set as the receiving apertures.

In the acoustic wave image generation apparatus according to an aspect of the present invention, furthermore, the receiving-aperture controlling unit desirably sets all the acoustic wave transducers arranged facing an entire part of the region of interest as the receiving apertures.

In the acoustic wave image generation apparatus according to an aspect of the present invention, furthermore, the receiving-aperture controlling unit may set only a part of the acoustic wave transducers arranged facing an entire part of the region of interest as the receiving apertures.

In the acoustic wave image generation apparatus according to an aspect of the present invention, furthermore, the receiving-aperture controlling unit desirably sets the part of the acoustic wave transducers in such a manner that the part of the acoustic wave transducers are located more closely at positions facing a center portion of the region of interest than at positions facing end portions of the region of interest.

Furthermore, the acoustic wave image generation apparatus according to an aspect of the present invention desirably further includes means for determining signals output from acoustic wave transducers among the plurality of acoustic wave transducers arranged facing the entire part of the region of interest, other than the part of the acoustic wave transducers, by interpolating signals output from the part of the acoustic wave transducers.

On the other hand, an acoustic wave image generation method according to an aspect of the present invention is an acoustic wave image generation method for generating a photoacoustic image on the basis of signals obtained by detecting, using an acoustic wave detection probe, photoacoustic waves produced from within a subject that has received light emitted to the subject and for generating a Doppler image concerning the subject, the acoustic wave image generation method including:

setting a region of interest in the Doppler image; and setting receiving apertures of the acoustic wave detection probe for detecting the photoacoustic waves to apertures smaller than all receiving apertures that the acoustic wave detection probe has, on the basis of a size of the set region of interest, and setting positions of the receiving apertures of the acoustic wave detection probe for detecting the photoacoustic waves, on the basis of a position of the set region of interest.

In the acoustic wave image generation method according to an aspect of the present invention, desirably, as the acoustic wave detection probe, an acoustic wave detection probe configured such that a plurality of acoustic wave transducers capable of detecting the photoacoustic waves are arranged is used, and the receiving apertures is set by blocking photoacoustic wave detection signals output from at least a part of acoustic wave transducers other than acoustic wave transducers to be set as the receiving apertures.

In the acoustic wave image generation method according to an aspect of the present invention, furthermore, all the acoustic wave transducers arranged facing an entire part of the region of interest are desirably set as the receiving apertures.

In the acoustic wave image generation method according to an aspect of the present invention, furthermore, only a part of the acoustic wave transducers arranged facing an entire part of the region of interest may be set as the receiving apertures.

In the acoustic wave image generation method according to an aspect of the present invention, furthermore, the part of the acoustic wave transducers are desirably set in such a manner that the part of the acoustic wave transducers are located more closely at positions facing a center portion of the region of interest than at positions facing end portions of the region of interest.

In the acoustic wave image generation method according to an aspect of the present invention, furthermore, signals output from acoustic wave transducers among the plurality of acoustic wave transducers arranged facing the entire part of the region of interest, other than the part of the acoustic wave transducers, are desirably determined by interpolating signals output from the part of the acoustic wave transducers.

According to an acoustic wave image generation apparatus according to an aspect of the present invention, a frame rate at which a photoacoustic image is generated can be maintained high.

BRIEF DESCRIPTION OF THE DRAWINGS

Exemplary embodiments according to the technique of the present disclosure will be described in detail based on the following figures, wherein.

DETAILED DESCRIPTION

An embodiment of the present invention will be described in detail hereinafter with reference to the drawings.

Figure 1:
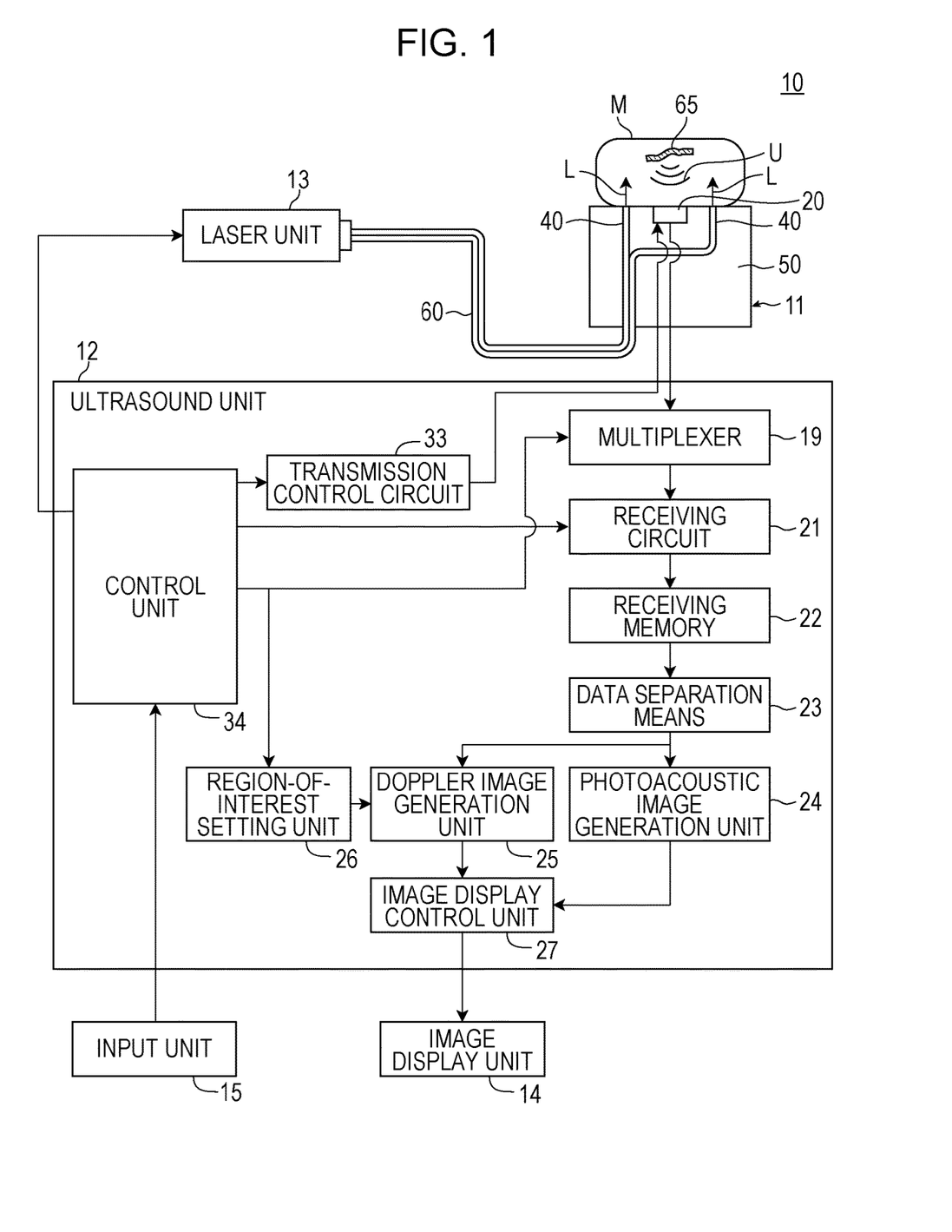
FIG. 1 is a schematic diagram illustrating an overall configuration of an acoustic wave image generation apparatus according to an embodiment of the present invention.

FIG. 1 is a schematic diagram illustrating an overall configuration of an acoustic wave image generation apparatus 10 according to an embodiment of the present invention. FIG. 1 schematically illustrates the shape of an acoustic wave detection probe (hereinafter referred to simply as a probe) 11. The acoustic wave image generation apparatus 10 in this example has a function of generating a photoacoustic image on the basis of photoacoustic wave detection signals, by way of example. As schematically illustrated in FIG. 1, the acoustic wave image generation apparatus 10 includes the probe 11, an ultrasound unit 12, a laser unit 13, an image display unit 14, and an input unit 15. The following sequentially describes these components.

The probe 11 has a function of emitting measurement light and ultrasonic waves to a subject M, which is, for example, a living body, and a function of detecting acoustic waves U propagating within the subject M. That is, the probe 11 can emit (transmit) ultrasonic waves (acoustic waves) to the subject M and detect (receive) reflected ultrasonic waves (reflected acoustic waves) reflected and returning from the subject M.

As used herein, the term "acoustic wave" includes an ultrasonic wave or ultrasound and a photoacoustic wave. The term "ultrasonic wave" or "ultrasound" refers to an elastic wave transmitted by the probe 11 and a reflected wave (reflected ultrasonic wave or reflected ultrasound) thereof, and the term "photoacoustic wave" refers to an elastic wave generated by an absorbing body 65 absorbing measurement light. Further, acoustic waves emitted from the probe 11 are not limited to ultrasonic waves but may be acoustic waves of audible frequencies if appropriate frequencies are selected in accordance with the object being examined, the measurement conditions, and so on. Note that examples of the absorbing body 65 in the subject M include blood vessels and a metal member.

The probe 11 is typically implemented by preparing probes for sector scanning, linear scanning, convex scanning, and so on and selecting and using an appropriate one of them in accordance with the part to be imaged. Further, an optical fiber 60 is connected to the probe 11. The optical fiber 60 serves as a connection unit that directs laser light L emitted from the laser unit 13 described below, which is measurement light, to light emission units 40.

The probe 11 includes a transducer array 20, two light emission units 40, and a housing 50. The transducer array 20 is an acoustic wave detector. The two light emission units 40 are disposed on both sides of the transducer array 20 with the transducer array 20 interposed therebetween in such a manner that each of the light emission units 40 is disposed on either side. The housing 50 accommodates the transducer array 20, the two light emission units 40, and so on.

In this embodiment, the transducer array 20 also functions as an ultrasonic wave transmitting element. The transducer array 20 is connected to a circuit for transmitting ultrasonic waves, a circuit for receiving acoustic waves, and so on via wiring (not illustrated).

The transducer array 20 is configured such that a plurality of acoustic wave transducers (ultrasonic transducers), which are electroacoustic transducer elements, are arranged in a one-dimensional direction. The acoustic wave transducers are, for example, piezoelectric elements composed of piezoelectric ceramic. The acoustic wave transducers may be piezoelectric elements fabricated from polymer films such as polyvinylidene fluoride (PVDF) films. The acoustic wave transducers have a function of converting the received acoustic waves U into electrical signals. Note that the transducer array 20 may include an acoustic lens.

As described above, the transducer array 20 in this embodiment is configured such that a plurality of acoustic wave transducers are arranged one-dimensionally. Alternatively, a transducer array configured such that a plurality of acoustic wave transducers are arranged two-dimensionally may be used.

As described above, the acoustic wave transducers also have a function of transmitting ultrasonic waves. That is, when alternating voltages are applied to the acoustic wave transducers, the acoustic wave transducers generate ultrasonic waves of frequencies corresponding to the frequencies of the alternating voltages. Note that transmission of ultrasonic waves and reception of ultrasonic waves may be separated from each other. That is, for example, ultrasonic waves may be transmitted from a position different from that of the probe 11 and reflected ultrasonic waves that result from the transmitted ultrasonic waves may be received by the probe 11.

The light emission units 40 are portions that emit the laser light L directed through the optical fiber 60 to the subject M. In this embodiment, the light emission units 40 are constituted by tip portions of the optical fiber 60, that is, end portions farther away from the laser unit 13 serving as a light source of the measurement light. As illustrated in FIG. 1, in this embodiment, two light emission units 40 are arranged on both sides of the transducer array 20 in an elevation direction thereof for example, with the transducer array 20 interposed therebetween. The elevation direction is a direction at a right angle to the direction of arrangement of a plurality of acoustic wave transducers and parallel to the detection surface of the transducer array 20 when the plurality of acoustic wave transducers are one-dimensionally arranged.

Each light emission unit may be fabricated from a light guide plate and a diffusion plate that are optically coupled to a tip of the optical fiber 60. The light guide plate can be fabricated from, for example, an acrylic plate or a quartz plate. As the diffusion plate, a lens diffusion plate configured such that microlenses are randomly arranged on a substrate can be used. For example, a quartz plate or the like with dispersed diffusing particles can be used. As the lens diffusion plate, a holographic diffusion plate or an engineering diffusion plate may be used.

The laser unit 13 illustrated in FIG. 1 has, for example, a Q-switched flash lamp-pumped solid-state laser such as a Q-switched alexandrite laser and emits the laser light L as measurement light. The laser unit 13 is configured to output the laser light L in response to receipt of a trigger signal from a control unit 34 of the ultrasound unit 12, for example. The laser unit 13 preferably outputs pulsed laser light L having a pulse width of 1 to 100 nsec (nanoseconds).

The wavelength of the laser light L is selected as appropriate in accordance with the light absorption properties of the absorbing body 65 in the subject M to be measured. For example, when the object to be measured is hemoglobin in a living body, that is, when blood vessels are to be imaged, the wavelength is typically preferably a wavelength within a near-infrared wavelength range. The term "near-infrared wavelength range" refers to a wavelength range of about 700 to 850 nm. However, the wavelength of the laser light L is not of course limited to this. The laser light L may be of a single wavelength or may include a plurality of wavelengths such as 750 nm and 800 nm. When the laser light L includes a plurality of wavelengths, beams of light of these wavelengths may be emitted simultaneously or may be switched alternately and emitted.

Note that the laser unit 13 can be configured, instead of using an alexandrite laser described above, using a YAG-SHG (Second harmonic generation)-OPO (Optical Parametric Oscillation) laser, which is also capable of outputting laser light in the near-infrared wavelength range, or using a Ti-Sapphire (titanium-sapphire) laser or the like.

The optical fiber 60 directs the laser light L emitted from the laser unit 13 to the two light emission units 40. The optical fiber 60 is not particularly limited and can be implemented using a well-known fiber such as a quartz fiber. For example, a single thick optical fiber may be used or a bundle fiber, which is made by bundling a plurality of optical fibers, may be used. As an example, when a bundle fiber is used, the bundle fiber is arranged such that the laser light L can enter from light incidence end surfaces of fiber portions collected into a single unit, and the respective tip portions of two branching fiber portions of the bundle fiber constitute the light emission units 40, as described above.

The ultrasound unit 12 includes a multiplexer 19, a receiving circuit 21, a receiving memory 22, data separation means 23, a photoacoustic image generation unit 24, a Doppler image generation unit 25, a region-of-interest setting unit 26, an image display control unit 27, a transmission control circuit 33, and the control unit 34. The ultrasound unit 12 typically has a processor, a memory, a bus, and so on. In the ultrasound unit 12, a program concerning the generation of a photoacoustic image and the generation of a Doppler image is incorporated in the memory. The program described above is activated by the control unit 34, which is constituted by the processor, to implement the functions of the photoacoustic image generation unit 24, the Doppler image generation unit 25, the region-of-interest setting unit 26, and the image display control unit 27. That is, these components are constituted by the memory in which the program is incorporated and the processor.

Note that the hardware configuration of the ultrasound unit 12 is not particularly limited and can be implemented by combining a plurality of ICs (Integrated Circuits), a processor, an ASIC (Application Specific Integrated Circuit), an FPGA (Field-programmable Gate Array), a memory, and so on as appropriate.

The control unit 34 is configured to control each unit of the acoustic wave image generation apparatus 10. In this embodiment, the control unit 34 includes a trigger control circuit (not illustrated). For example, the trigger control circuit sends an optical trigger signal to the laser unit 13 when generating a photoacoustic image. Thus, a flash lamp serving as an excitation source is turned on in the Q-switched solid-state laser of the laser unit 13, and excitation of a laser rod is started. While the laser rod is maintained in an excited state, the laser unit 13 is in a state of being able to output the laser light L.

Thereafter, the control unit 34 transmits a Q-switch trigger signal from the trigger control circuit to the laser unit 13. That is, the control unit 34 controls the output timing of the laser light L from the laser unit 13 by using the Q-switch trigger signal. Further, at the same time as transmitting the Q-switch trigger signal, the control unit 34 transmits a sampling trigger signal to the receiving circuit 21. The sampling trigger signal specifies the timing when an AD converter (Analog to Digital convertor) of the receiving circuit 21 starts sampling photoacoustic wave detection signals. The use of a sampling trigger signal in this way makes it possible to sample photoacoustic wave detection signals in synchronization with the output of the laser light L.

When generating an ultrasound image, the control unit 34 transmits an ultrasonic trigger signal to the transmission control circuit 33 to provide an instruction to transmit ultrasonic waves. Upon receipt of the ultrasonic trigger signal, the transmission control circuit 33 causes the probe 11 to transmit ultrasonic waves. The control unit 34 transmits a sampling trigger signal to the receiving circuit 21 in accordance with the timing of transmission of ultrasonic waves to start sampling reflected ultrasonic detection signals.

When the photoacoustic image or ultrasound image described above is to be generated, the subject M is scanned by the laser light L or ultrasonic waves, with the position of the probe 11 being slightly displaced with respect to the subject M in, for example, the elevation direction described above. Accordingly, the photoacoustic wave detection signals or reflected ultrasonic detection signals described above are sampled in synchronization with the scanning of the subject M, with the acoustic wave detection lines being shifted one by one. The scanning of the subject M may be performed by a technician manually moving the probe 11 or by using an automatic scanning mechanism.

The receiving circuit 21 receives photoacoustic wave detection signals output from the transducer array 20 of the probe 11, and stores the received detection signals in the receiving memory 22. Note that the photoacoustic wave detection signals are propagated to the receiving circuit 21 through the multiplexer 19. The multiplexer 19 will be described in detail below.

The receiving circuit 21 typically includes a low-noise amplifier, a variable-gain amplifier, a low-pass filter, and an AD converter. The photoacoustic wave detection signals output from the probe 11 are amplified by the low-noise amplifier and are then subjected to gain adjustment by the variable-gain amplifier in accordance with the depth. The resulting photoacoustic wave detection signals, after the high-frequency components have been removed by the low-pass filter, are converted into digital signals by the AD converter, and the digital signals are stored in the receiving memory 22.

The receiving circuit 21 is constituted by, for example, one IC (Integrated Circuit). The removal of the high-frequency components by the low-pass filter described above is performed in order to prevent the occurrence of folding noise during AD conversion, with the cutoff frequency being typically about 10 MHz to 30 MHz, which is about half the sampling frequency in AD conversion.

In this embodiment, the probe 11 outputs photoacoustic wave detection signals and reflected ultrasonic detection signals. Thus, the receiving memory 22 stores digitized photoacoustic wave detection signals and reflected ultrasonic detection signals. More specifically, the photoacoustic wave detection signals described above are signals obtained by detecting photoacoustic waves generated from within the subject M which has absorbed the laser light L emitted to the subject M. In contrast, the reflected ultrasonic detection signals described above are signals obtained by detecting reflected acoustic waves, which are ultrasonic waves, or acoustic waves, emitted to the subject M and reflected within the subject M.

The data separation means 23 reads out data for a photoacoustic image, that is, the digitized photoacoustic wave detection signals, from the receiving memory 22 and transmits the photoacoustic wave detection signals to the photoacoustic image generation unit 24. Further, the data separation means 23 reads out data for a reflected ultrasound image, that is, the digitized reflected ultrasonic detection signals, from the receiving memory 22 and transmits the reflected ultrasonic detection signals to the Doppler image generation unit 25.

The photoacoustic image generation unit 24 reconstructs the photoacoustic wave detection signals received from the receiving memory 22 via the data separation means 23 and generates a photoacoustic image. Specifically, the photoacoustic image generation unit 24 adds together photoacoustic wave detection signals based on signals from the individual acoustic wave transducers of the transducer array 20 at delay times corresponding to the respective positions of the acoustic wave transducers and generates photoacoustic wave detection signals for one line (delay-and-sum method). The photoacoustic image generation unit 24 may perform reconstruction by using the CBP method (Circular Back Projection) instead of using the delay-and-sum method. Alternatively, the photoacoustic image generation unit 24 may perform reconstruction by using Hough transformation or Fourier transformation. The reconstructed photoacoustic wave detection signals for a plurality of lines undergo signal processing such as detection processing and log conversion processing and are then sent to the image display unit 14 via the image display control unit 27 as signals for displaying a photoacoustic image (tomographic image) of a certain cross-section of the subject M.

The Doppler image generation unit 25 performs frequency analysis of velocity information from the reflected ultrasonic detection signals received from the receiving memory 22 via the data separation means 23, extracts blood flow, tissues, and contrast medium echo components by using the Doppler effect, and acquires a Doppler image signal for displaying a Doppler image indicating, for example, blood flow portions. The Doppler image signal is also sent to the image display unit 14 via the image display control unit 27.

The area for which the Doppler image signal described above is acquired is set by a technician. This area is referred to as a region of interest. The position and size of the region of interest are set by the region-of-interest setting unit 26. In this embodiment, by way of example, a Doppler image that can be generated from all of the reflected ultrasonic detection signals received from the receiving memory 22 is first displayed on the image display unit 14. While observing the Doppler image, a technician sets a smaller image area indicating, for example, blood flow portions as a region of interest.

The setting of a region of interest is performed as follows. The technician designates a region in the Doppler image displayed on the image display unit 14 by using, for example, the input unit 15 such as a mouse, and the designated region is input to the control unit 34. Then, the control unit 34 sends information indicating the designated region of interest to the region-of-interest setting unit 26 to control the region-of-interest setting unit 26.

The setting of a region of interest may be performed by, instead of, as described above, first generating a Doppler image of a wide area and then designating a region, generating an ultrasound B mode image from the reflected ultrasonic detection signals output from the receiving memory 22, displaying the ultrasound B mode image on the image display unit 14, and designating a region in the B mode image.

The image display control unit 27 causes the image display unit 14 to display a photoacoustic image on the basis of the signals described above for displaying a photoacoustic image and display a Doppler image on the basis of the Doppler image signal described above. These two types of images are separately displayed on the image display unit 14 or are combined into a composite image which is displayed on the image display unit 14. In the latter case, for example, the image display control unit 27 superimposes the photoacoustic image and the Doppler image on each other to combine the images.

Figure 8:
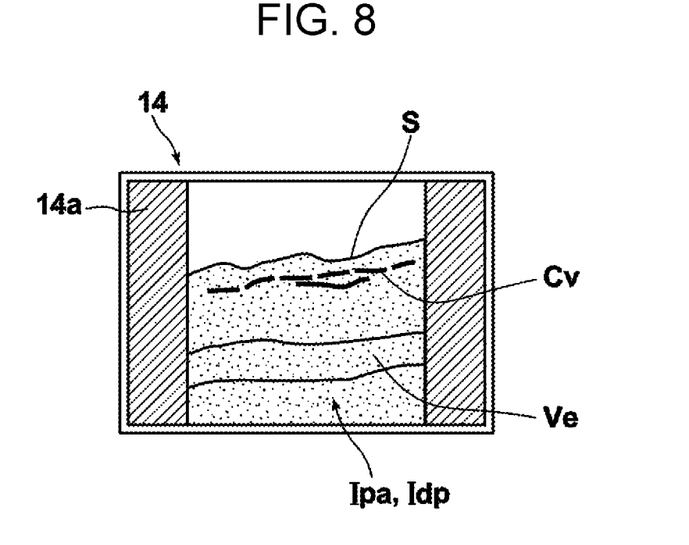
FIG. 8 is a schematic diagram illustrating a state in which a Doppler image and a photoacoustic image are displayed superimposed on each other.

FIG. 8 schematically illustrates a state in which a photoacoustic image Ipa and a Doppler image Idp are displayed superimposed on each other on a display screen 14a of the image display unit 14. The photoacoustic image Ipa shows a capillary vessel Cv and so on present in a portion comparatively close to a skin surface S of the subject M. In contrast, the Doppler image Idp shows a blood flow portion Ve at a position deeper than the capillary vessel Cv.

The two types of acoustic wave images described above are generated with a time interval. In this embodiment, in particular, a photoacoustic image is generated after a Doppler image has been generated. In order to display these acoustic wave images in a superimposed manner, for example, the image display control unit 27 includes a buffer memory for temporarily storing an image signal indicating each image.

Figure 2:
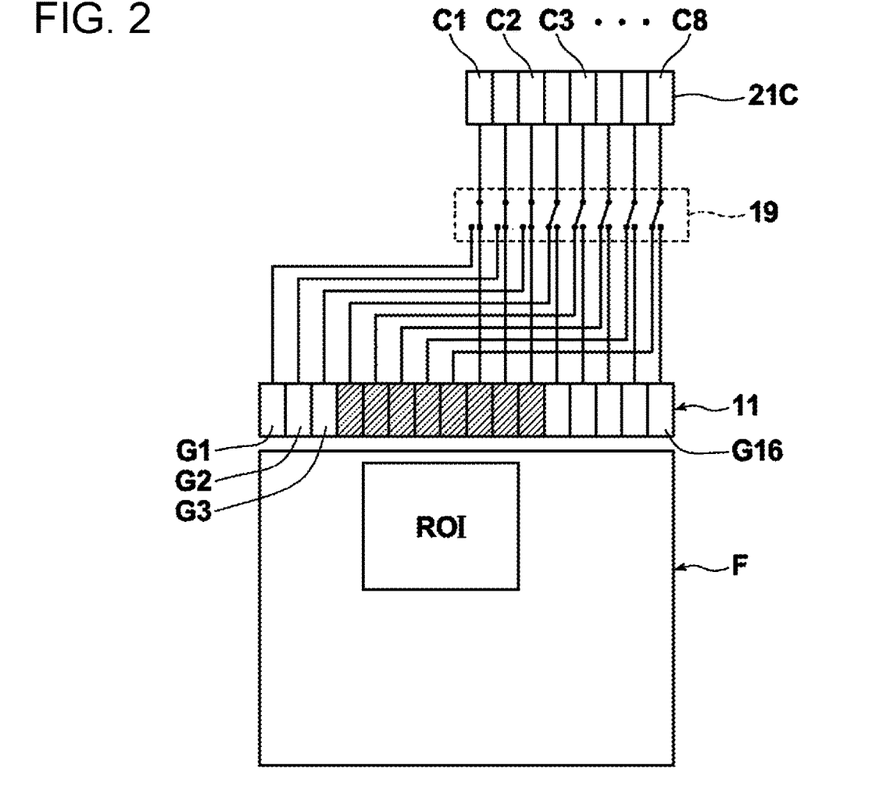
FIG. 2 is a schematic diagram illustrating an example setting of receiving apertures of an acoustic wave detection probe.

Next, control of receiving apertures of the probe 11 illustrated in FIG. 1 for the creation of a photoacoustic image will be described. FIG. 2 is a schematic diagram used for this description and illustrates the probe 11, which is configured such that a plurality of acoustic wave transducers G1 to G16 are arranged in a one-dimensional array. That is, this example illustrates the probe 11 as a 16-channel probe. Note that the acoustic wave transducers G1 to G16 correspond to the transducer array 20 illustrated in FIG. 1. While some of the acoustic wave transducers G1 to G16 are marked with the numbers in FIG. 2, the acoustic wave transducer G1, the acoustic wave transducer G2, . . . , and the acoustic wave transducer G16 are assumed to be arranged in this order from left to right in FIG. 2.

Furthermore, F represents a field in which a Doppler image can be generated, and ROI represents a region of interest set in the field F. While the position of the probe 11 is represented as a position relative to the field F here, the relative position corresponds to a positional relationship between the probe 11 and the subject M when a photoacoustic image is to be generated.

Furthermore, 21C conceptually represents receiving channels of the receiving circuit 21 illustrated in FIG. 1. Here, the receiving circuit 21 is assumed to have eight receiving channels C1 to C8. Further, 19 represents the multiplexer (see FIG. 1) disposed between the receiving channels 21C and the probe 11.

In the configuration described above, when the receiving circuit 21 is to receive all of the signals output from the 16-channel acoustic wave transducers G1 to G6, first, the signals output from the 8-channel acoustic wave transducers G1 to G8 are received by the receiving circuit 21 through the eight receiving channels C1 to C8. Thereafter, the multiplexer 19 is switched and the signals output from the remaining 8-channel acoustic wave transducers G9 to G16 are received by the receiving circuit 21 through the eight receiving channels C1 to C8.

Here, when a photoacoustic image is to be generated, the multiplexer 19 is brought into the state illustrated in FIG. 2. Then, in order to generate a photoacoustic image of a certain cross-section of the subject M, the laser light L is emitted to the subject M once in this state. When the laser light L is emitted once in this way, only the signals (photoacoustic wave detection signals) output from the 8-channel acoustic wave transducers G4 to G11 are received by the receiving circuit 21 through the eight receiving channels C1 to C8. Thereafter, the multiplexer 19 is not switched and the reception of photoacoustic wave detection signals for generating a photoacoustic image of the cross-section is completed.

As described above, in this example, signals (photoacoustic wave detection signals) output from a part of the 16-channel acoustic wave transducers G1 to G6, namely, the 8-channel acoustic wave transducers G1 to G3 and G12 to G16, are blocked by the multiplexer 19 and are not received by the receiving circuit 21. Thus, the frame rate at which a photoacoustic image is generated can be increased to improve the real-time acquisition of a photoacoustic image. In FIG. 2, acoustic wave transducers to be set as the receiving apertures are indicated by hatching (also in FIG. 4 to FIG. 7).

The 8-channel acoustic wave transducers G4 to G1 to be set as the receiving apertures described above are determined on the basis of the size and position of the region of interest ROI, which is an area for which a Doppler image signal is acquired. That is, in this example, the 8-channel acoustic wave transducers G4 to G11 are set as the receiving apertures so that all of the acoustic wave transducers arranged facing an entire part of the region of interest ROI can be set as the receiving apertures.

Figure 3:
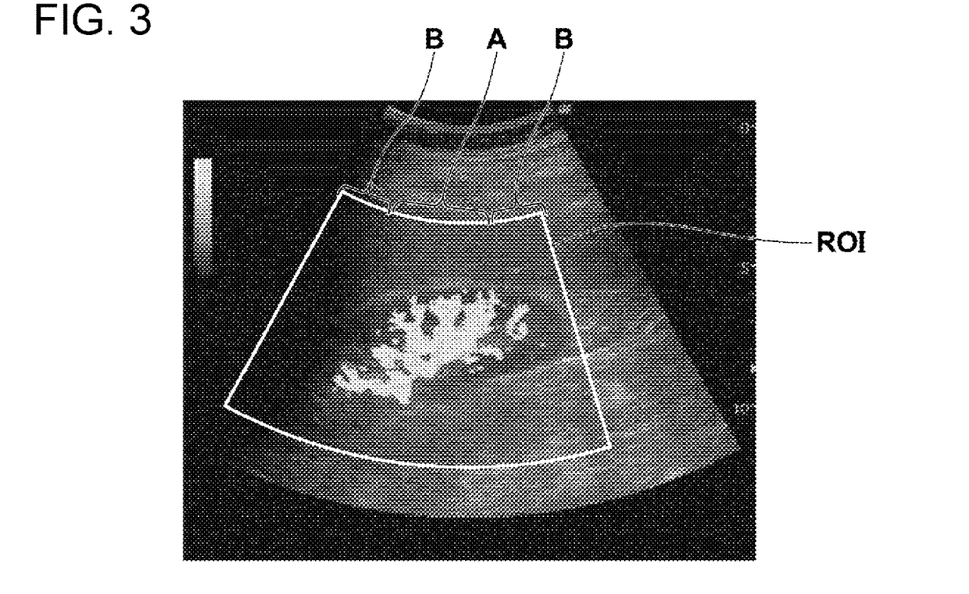
FIG. 3 is a schematic diagram illustrating an example setting of a region of interest.

Here, the setting of the receiving apertures will be described with reference to an actual ultrasound image illustrated in FIG. 3. In FIG. 3, an arc-shaped portion in a black background is an ultrasound image such as a B mode image, and the region of interest ROI, which is a display area of a Doppler image, is set in the ultrasound image. In the example in FIG. 3, blood flow portions appear in the vicinity of a center portion of the region of interest ROI, which is indicated by A, and no object to be displayed is present in portions indicated by B near the left and right end portions of the region of interest in FIG. 3.

A Doppler image typically shows blood flow portions. Further, in many cases, a photoacoustic image is used to display blood vessel portions that well absorb light such as the laser light L and that generate photoacoustic waves. Thus, on the basis of the assumption that the region of interest ROI is set to include the blood flow portions described above, the receiving apertures of the probe 11 are set so that photoacoustic wave detection signals can be generated for at least the region of interest ROI. This enables blood vessel portions to be displayed on a generated photoacoustic image as described above even if the receiving apertures are restricted to be small.

Note that the state of the multiplexer 19 is controlled by the control unit 34 on the basis of information indicating the region of interest ROI. That is, in this embodiment, the multiplexer 19 and the control unit 34 constitute receiving-aperture control means. In addition, the region-of-interest setting unit 26 and the control unit 34 constitute means for setting a region of interest.

Figure 4:
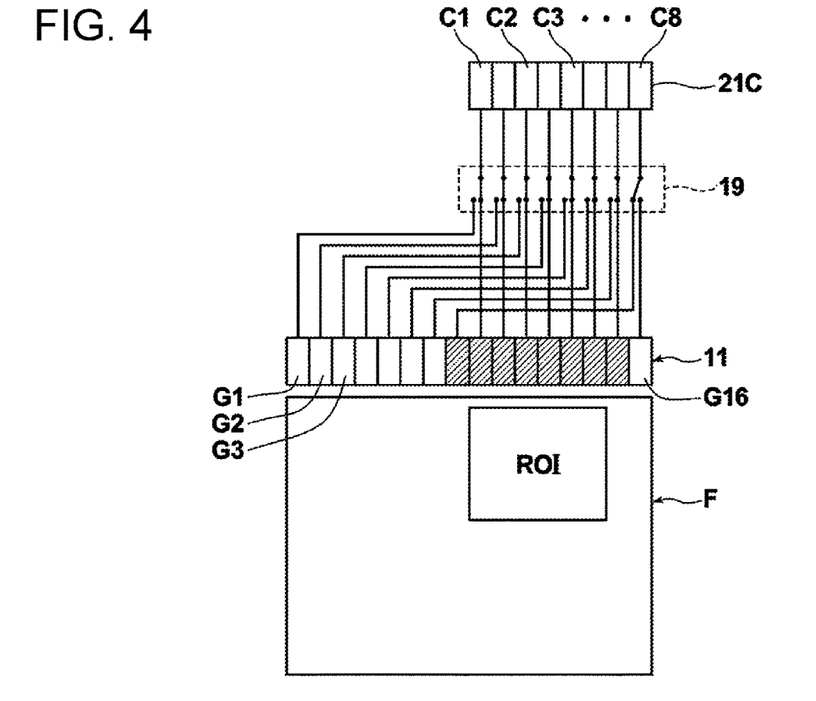
FIG. 4 is a schematic diagram illustrating another example setting of receiving apertures of the acoustic wave detection probe.

Next, FIG. 4 illustrates another example setting of receiving apertures of the probe 11. In this example, the size of the receiving apertures is assumed to correspond to 8 channels, as in the example in FIG. 2; however, the position of the region of interest ROI is different from that in the example in FIG. 2. In accordance with the position of the region of interest ROI, the acoustic wave transducers G8 to G15 are set as receiving apertures.

In the following, the effects described above will be described in more detail with reference to an example using an actual apparatus. In this example, it is assumed that the probe 11 includes 128-channel acoustic wave transducers, the receiving circuit 21 has 64 receiving channels, and the laser light L is emitted at a repetition frequency of 10 Hz. In this example, in order to generate one photoacoustic image, the laser light L typically needs to be emitted twice such that
(1) the laser light L is emitted (first time),
(2) 64-channel acoustic wave transducers detect photoacoustic waves (first time),
(3) the laser light L is emitted (second time),
(4) the remaining 64-channel acoustic wave transducers detect photoacoustic waves (second time), and
(5) the photoacoustic image generation unit 24 (see FIG. 1) generates a photoacoustic image. Since the laser light L is emitted at a repetition frequency of 10 Hz, the repetition frequency for photoacoustic image generation is 5 Hz (with the frame rate being 5 images/second).

In contrast, basically as in the example in FIG. 2, when half the original 128-channel acoustic wave transducers of the probe 11, namely, 64-channel acoustic wave transducers, are to be set as the receiving apertures, in order to generate one photoacoustic image, it is only required to emit the laser light L once such that
(1) the laser light L is emitted (first time),
(2) the 64-channel acoustic wave transducers detect photoacoustic waves (first time), and
(3) the photoacoustic image generation unit 24 (see FIG. 1) generates a photoacoustic image. Thus, the repetition frequency for photoacoustic image generation can be 10 Hz (with the frame rate being 10 images/second), which is equal to the repetition frequency at which the laser light L is emitted.

In general, the region of interest ROI is often set in a partial region within an area in which an ultrasound image can be acquired by the probe 11. Thus, a photoacoustic image that can display desired portions such as blood vessel portions can be often generated even if the number of receiving apertures of the probe 11 is limited to about half the original number of receiving apertures of the probe 11. According to the present invention, therefore, in many cases, as described above, the frame rate in photoacoustic image generation can be improved compared with when all of the receiving apertures originally included in the probe 11 are used.

Furthermore, a shallow region can typically be visualized in a photoacoustic image. That is, only a portion present comparatively close to a surface of the subject on the side irradiated with light can be visualized. Thus, in many cases, photoacoustic wave detection signals output from acoustic wave transducers facing portions away from the region of interest ROI in a Doppler image do not contribute to improvement in image quality because the acoustic wave transducers have deep receive directivity angles, but rather may increase noise and thus deteriorate the quality of the photoacoustic image. In the example illustrated in FIG. 2 or the example illustrated in FIG. 4, in contrast, a photoacoustic image is generated on the basis of mainly signals output from acoustic wave transducers having shallow receive directivity angles, and thus an improvement in the quality of the photoacoustic image can be expected.

If the region of interest ROI is comparatively small and the number of channels of acoustic wave transducers corresponding to set receiving apertures of the probe 11 is smaller than 64, the receiving apertures may be expanded unless the frame rate is reduced. For example, when the number of channels of acoustic wave transducers corresponding to receiving apertures of the probe 11 determined on the basis of the region of interest ROI in a Doppler image is 32, the receiving apertures may be expanded to 64 channels.

Next, another example setting of receiving apertures of the probe 11 will be described with reference to FIG. 5. In the example illustrated in FIG. 2 and the example illustrated in FIG. 4, all of the acoustic wave transducers arranged facing an entire part of the region of interest ROI are set as receiving apertures. However, when the region of interest ROI is comparatively large (long in the direction of arrangement of the acoustic wave transducers), the setting of receiving apertures in the manner as in the two examples described above may result in the number of receiving apertures being larger than the number of receiving channels C1 to C8 of the receiving circuit 21. In this case, the frame rate at which a photoacoustic image is generated is reduced.

Figure 5:
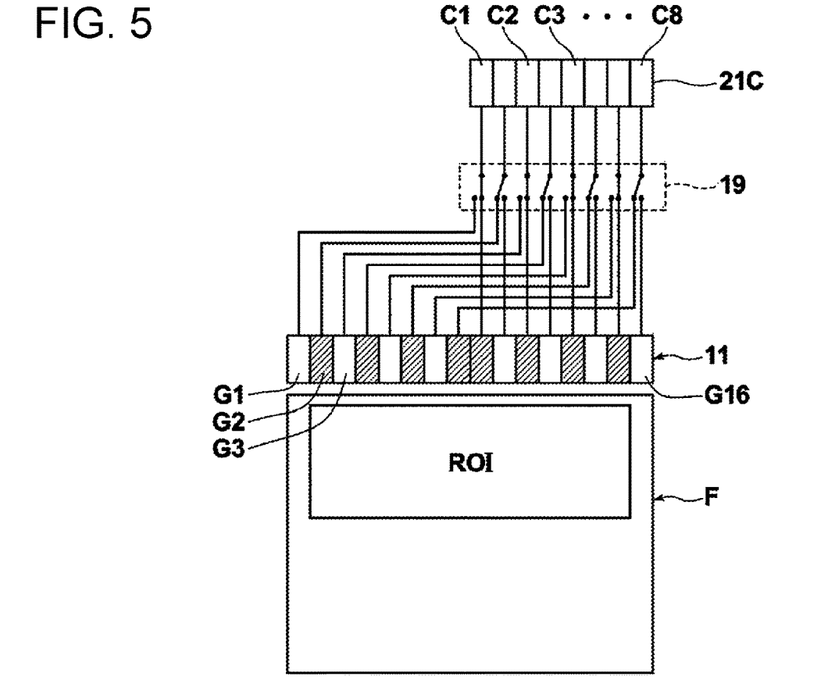
FIG. 5 is a schematic diagram illustrating still another example setting of receiving apertures of the acoustic wave detection probe.

To prevent this situation, in the example in FIG. 5, only a part of the acoustic wave transducers arranged facing an entire part of the region of interest ROI are set as receiving apertures. That is, in this example, specifically, only eight acoustic wave transducers G2. G4, G6, G8, G9, G11, G13, and G15 among 14 acoustic wave transducers arranged facing an entire part of the region of interest ROI are set as receiving apertures. Thus, the number of receiving apertures of the probe 11 can be made equal to the number of receiving channels C1 to C8 of the receiving circuit 21, which can prevent a reduction in the frame rate at which a photoacoustic image is generated. This effect is also obtained in an example in FIG. 6 described below.

The setting of receiving apertures of the probe 11 described above is also applicable to the previously described example using an actual apparatus, that is, the example in which the probe 11 includes 128-channel acoustic wave transducers, the receiving circuit 21 has 64 receiving channels, and the laser light L is emitted at a repetition frequency of 10 Hz. In this case, the repetition frequency for photoacoustic image generation can be 10 Hz, which is equal to the repetition frequency at which the laser light L is emitted.

Figure 6:
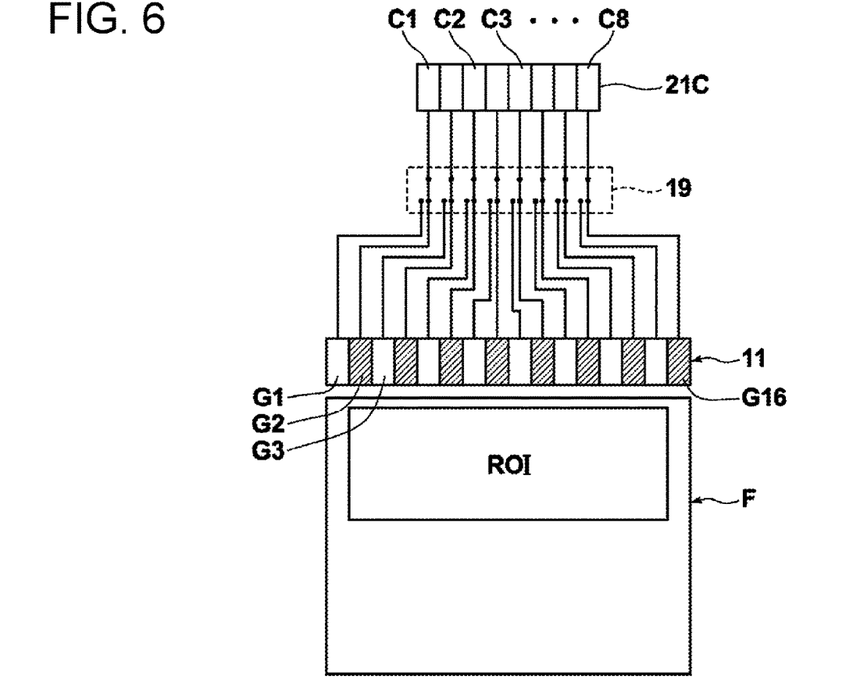
FIG. 6 is a schematic diagram illustrating still another example setting of receiving apertures of the acoustic wave detection probe.

FIG. 6 illustrates still another example setting of receiving apertures of the probe 11. The example illustrated in FIG. 6 is basically the same as the example illustrated in FIG. 5, except that a part of the acoustic wave transducers to be set as receiving apertures are arranged in a different manner.

In the example in FIG. 5 and the example in FIG. 6 described above, it is desirable to determine signals (photoacoustic wave detection signals) output from acoustic wave transducers not set as receiving apertures among a plurality of acoustic wave transducers arranged facing an entire part of the region of interest ROI by interpolating signals output from acoustic wave transducers set as the receiving apertures. A photoacoustic image is generated on the basis of the signals determined as a result of interpolation. Therefore, a photoacoustic image having brightness or density distribution without unpleasant sensation can be generated.

The interpolation described above may be performed on signals after the reconstruction of a photoacoustic image or may be performed on signals before the reconstruction of a photoacoustic image. For example, in the former case, the photoacoustic image generation unit 24 illustrated in FIG. 1 may have an interpolation function, and the photoacoustic image generation unit 24 may be used as interpolation means.

Figure 7:
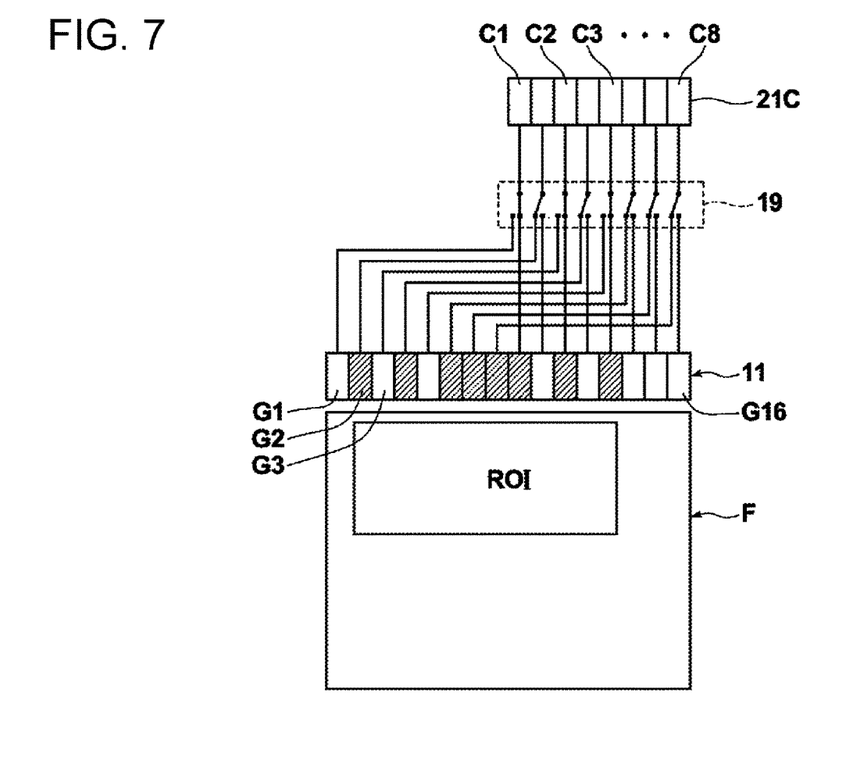
FIG. 7 is a schematic diagram illustrating still another example setting of receiving apertures of the acoustic wave detection probe.

FIG. 7 illustrates still another example setting of receiving apertures of the probe 11. In the example illustrated in FIG. 7, as in the example in FIG. 5 and the example in FIG. 6 described above, only a part of acoustic wave transducers arranged facing an entire part of the region of interest ROI, namely, acoustic wave transducers G2, G4, G6, G7, G8, G9, G11, and G13, are set as receiving apertures. Thus, effects similar to those in the example in FIG. 5 and the example in FIG. 6 are obtained.

In addition to this, in the example in FIG. 7, the acoustic wave transducers G2, G4, G6, G7, G8, G9, G11, and G13 is selected as acoustic wave transducers to be set as receiving apertures. Thus, the acoustic wave transducers to be set as the receiving apertures are located more closely at positions facing the center portion of the region of interest ROI than at positions facing the end portions of the region of interest ROI.

Here, in general, it is common that the region of interest ROI is set so that blood flow portions or the like is located near the center portion thereof. In this case, a photoacoustic wave detection signal from an acoustic wave transducer nearer the edge portion of the region of interest ROI has a lower signal intensity which may cause noise to occur in a photoacoustic image after reconstruction. Accordingly, receiving apertures of the probe 11 are set as in this example, and signals obtained by detecting photoacoustic waves generated near the end portions of the region of interest ROI are used as little as possible for the generation of a photoacoustic image, thereby achieving the effect of improving the quality of the photoacoustic image.

The foregoing has described in detail the case where the number of channels (acoustic wave transducers) of the probe 11 is 128 and the number of receiving channels on the receiving circuit 21 side is 64, by way of example. In the present invention, however, the numbers of channels are not limited to those illustrated in the example above. For example, the number of channels of the probe 11 may be 196, 256, 512, or the like, and the number of receiving channels on the receiving circuit 21 side may be 128, 256, or the like.

In addition, the multiplexer 19 (see FIG. 1) may include three or more input systems. Furthermore, means other than the multiplexer 19 may be used as means for setting receiving apertures of the probe 11.

What is claimed is:

1. An acoustic wave image generation apparatus comprising:
a light emission unit that emits light to a subject;
an ultrasonic wave emission unit that emits an ultrasonic wave to the subject;
an acoustic wave detection probe that detects photoacoustic waves produced from within the subject that has received the light, and a reflected ultrasonic wave produced from within the subject that has received the ultrasonic wave;
a Doppler image generation unit that generates a Doppler image based on the detected reflected ultrasonic wave;
a photoacoustic image generation unit that generates a photoacoustic image based on the detected photoacoustic waves, a frame rate at which the photoacoustic image is generated being lower than a frame rate at which the Doppler image is generated;
a setting unit that sets a region of interest in the Doppler image; and
a receiving-aperture controlling unit that sets receiving apertures of the acoustic wave detection probe configured to detect the photoacoustic waves to apertures smaller than all receiving apertures that the acoustic wave detection probe has, on the basis of a size of the set region of interest, and for setting positions of the receiving apertures of the acoustic wave detection probe configured to detect the photoacoustic waves, on the basis of a position of the set region of interest.

2. The acoustic wave image generation apparatus according to claim 1, wherein as the acoustic wave detection probe, an acoustic wave detection probe configured such that a plurality of acoustic wave transducers capable of detecting the photoacoustic waves are arranged is used, and
wherein the receiving-aperture controlling unit blocks photoacoustic wave detection signals output from at least a part of acoustic wave transducers other than acoustic wave transducers to be set as a receiving apertures.

3. The acoustic wave image generation apparatus according to claim 2, wherein the receiving-aperture controlling unit sets all the acoustic wave transducers arranged facing an entire part of the region of interest as the receiving apertures.

4. The acoustic wave image generation apparatus according to claim 2, wherein the receiving-aperture controlling unit sets only a part of the acoustic wave transducers arranged facing an entire part of the region of interest as the receiving apertures.

5. The acoustic wave image generation apparatus according to claim 4, wherein the receiving-aperture controlling unit sets the part of the acoustic wave transducers in such a manner that the part of the acoustic wave transducers are located more closely at positions facing a center portion of the region of interest than at positions facing end portions of the region of interest.

6. The acoustic wave image generation apparatus according to claim 4, further comprising means for determining signals output from acoustic wave transducers among the plurality of acoustic wave transducers arranged facing the entire part of the region of interest, other than the part of the acoustic wave transducers, by interpolating signals output from the part of the acoustic wave transducers.

7. An acoustic wave image generation method comprising:
  emitting light to a subject;
  emitting an ultrasonic wave to the subject;
  detecting photoacoustic waves produced from within the subject that has received the light and a reflected ultrasonic wave produced from within the subject that has received the ultrasonic wave;
  generating a Doppler image based on the detected reflected ultrasonic wave;
  generating a photoacoustic image based on the detected photoacoustic waves, a frame rate at which the photoacoustic image is generated being lower than a frame rate at which the Doppler image is generated;
  setting a region of interest in the Doppler image;
  setting receiving apertures of the acoustic wave detection probe to apertures smaller than all receiving apertures that the acoustic wave detection probe has, on the basis of a size of the set region of interest, and setting positions of the receiving apertures of the acoustic wave detection probe, on the basis of a position of the set region of interest, and
  detecting the photoacoustic waves based on the set receiving apertures.

8. The acoustic wave image generation method according to claim 7, wherein as the acoustic wave detection probe, an acoustic wave detection probe configured such that a plurality of acoustic wave transducers capable of detecting the photoacoustic waves are arranged is used, and
  wherein the receiving apertures is set by blocking photoacoustic wave detection signals output from at least a part of acoustic wave transducers other than acoustic wave transducers to be set as the receiving apertures.

9. The acoustic wave image generation method according to claim 8, wherein all the acoustic wave transducers arranged facing an entire part of the region of interest are set as the receiving apertures.

10. The acoustic wave image generation method according to claim 8, wherein only a part of the acoustic wave transducers arranged facing an entire part of the region of interest are set as the receiving apertures.

11. The acoustic wave image generation method according to claim 10, wherein the part of the acoustic wave transducers are set in such a manner that the part of the acoustic wave transducers are located more closely at positions facing a center portion of the region of interest than at positions facing end portions of the region of interest.

12. The acoustic wave image generation method according to claim 10, wherein signals output from acoustic wave transducers among the plurality of acoustic wave transducers arranged facing the entire part of the region of interest, other than the part of the acoustic wave transducers, are determined by interpolating signals output from the part of the acoustic wave transducers.

* * * * *